United States Patent
Gronberg

(10) Patent No.: US 9,761,022 B1
(45) Date of Patent: Sep. 12, 2017

(54) ACCURATE REPRODUCTION OF CONVENTIONAL COMPUTED TOMOGRAPHY, CT, IMAGES FROM SPECTRAL CT DATA

(71) Applicant: Prismatic Sensors AB, Stockholm (SE)

(72) Inventor: Fredrik Gronberg, Stockholm (SE)

(73) Assignee: PRISMATIC SENSORS AB, Stockholm (SE)

( * ) Notice: Subject to any disclaimer, the term of this patent is extended or adjusted under 35 U.S.C. 154(b) by 0 days.

(21) Appl. No.: 15/430,760

(22) Filed: Feb. 13, 2017

Related U.S. Application Data

(63) Continuation of application No. PCT/SE2016/051277, filed on Dec. 16, 2016.

(51) Int. Cl.
*G06T 11/00* (2006.01)
*A61B 6/03* (2006.01)
*A61B 6/00* (2006.01)

(52) U.S. Cl.
CPC ......... *G06T 11/005* (2013.01); *A61B 6/032* (2013.01); *A61B 6/4241* (2013.01); *A61B 6/5211* (2013.01); *A61B 6/583* (2013.01); *G06T 2210/41* (2013.01)

(58) Field of Classification Search
USPC ............................................. 382/131
See application file for complete search history.

(56) References Cited

U.S. PATENT DOCUMENTS

| | | | |
|---|---|---|---|
| 8,183,535 B2 | 5/2012 | Danielsson et al. | |
| 8,309,910 B2 * | 11/2012 | Dutta | A61B 6/032 250/252.1 |
| 2004/0228451 A1 * | 11/2004 | Wu | A61B 6/583 378/207 |
| 2006/0023844 A1 * | 2/2006 | Naidu | G01N 23/046 378/210 |
| 2012/0093282 A1 * | 4/2012 | Kappler | A61B 6/032 378/18 |

(Continued)

OTHER PUBLICATIONS

Alvarez, R. E., et al., "Energy-Selective Reconstructions in X-Ray Computerized Tomography," Physics in Medicine and Biology, vol. 21, No. 5, 1976, pp. 733-744.

(Continued)

*Primary Examiner* — Gregory F Cunningham
(74) *Attorney, Agent, or Firm* — Young & Thompson

(57) ABSTRACT

A method and corresponding arrangement for reconstructing an image based on spectral image data acquired for at least two different effective energies includes: obtaining a first set of spectral image data related to an object to be imaged and a second set of spectral image data related to a calibration phantom including at least one reference material; performing basis decomposition based on the first set of spectral image data, providing estimated basis images of the object to be imaged with respect to associated basis functions; performing basis decomposition based on the second set of spectral image data, providing calibrated estimates of reference basis coefficients corresponding to the at least one reference material; and determining image values representing the object based on a system model of an imaging system to be emulated, the estimated basis images and their associated basis functions, and the calibrated estimates of reference basis coefficients.

19 Claims, 6 Drawing Sheets

(56) References Cited

U.S. PATENT DOCUMENTS

2012/0163557 A1* 6/2012 Hsieh ................... A61B 6/032
378/207
2016/0113603 A1* 4/2016 Schirra ................. A61B 6/032
250/252.1

OTHER PUBLICATIONS

Alvarez, R. E., Dimensionality and Noise in Energy Selective X-Ray Imaging, Medical Physics, vol. 40, No. 11, Nov. 2013, pp. 111909-1-111909-13.
Bornefalk, H., "Synthetic Hounsfield Units From Spectral CT Data," Physics in Medicine and Biology, vol. 57, 2012, pp. N83-N87.
Holmes, III, et al., "Evaluation of Non-Linear Blending in Dual-Energy Computed Tomography," European Journal of Radiology, vol. 68, No. 3, pp. 409-413.
Kim, K. S., et al., "Image Fusion in Dual Energy Computed Tomography for Detection of Hypervascular Liver Hepatocellular Carcinoma," Investigative Radiology, vol. 45, No. 3, Mar. 2010, pp. 149-157.
Schlomka, J.P., "Experimental Feasibility of Multi-Energy Photon-Counting K-Edge Imagining in Pre-Clinical Computer Tomography," Physics in Medicine and Biology, vol. 53, 2008, pp. 4031-4047.

\* cited by examiner

ACCURATE REPRODUCTION OF CONVENTIONAL COMPUTED TOMOGRAPHY, CT, IMAGES FROM SPECTRAL CT DATA

TECHNICAL FIELD

The proposed technology generally relates to x-ray imaging, and more specifically to a method for emulating or mimicking images produced by conventional x-ray detectors with data produced by new imaging technologies, in order to take advantage of the body of experience and knowledge in the field of radiology during a period of technological transition.

In particular, the proposed technology relates to a method and system for image reconstruction, a corresponding x-ray imaging system, a Computed Tomography, CT system and a corresponding computer program and computer-program product.

BACKGROUND

Radiographic imaging techniques such as x-ray imaging have been used for years in medical applications and for non-destructive testing.

Normally, an x-ray imaging system includes an x-ray source and an x-ray detector consisting of multiple detector elements. The x-ray source emits x-rays, which pass through a subject or object to be imaged and are then registered by the detector. Since some materials absorb a larger fraction of the x-rays than others, an image is formed of the subject or object.

Conventional x-ray detectors are energy integrating, the contribution from each detected photon to the detected signal is therefore proportional to its energy, and in conventional CT, measurements are acquired for a single effective energy. The images produced by a conventional CT system therefore have a certain look, where different tissues and materials show typical values in certain ranges. Spectral CT is a collective term for CT imaging technologies that acquire measurement data at multiple effective energies. The energy information in spectral CT data allows for new kinds of images to be created, where new information is available and image artifacts inherent to conventional technology can be removed.

In order to draw upon the knowledge and rules-of-thumb accumulated from years of experience using conventional equipment, it would be desirable to along with new images, produce a single image from spectral CT data that mimics the characteristics of conventional CT images.

In the prior art there exist methods that use image-blending techniques for other purposes, such as optimizing contrast-to-noise ratio or detectability for a given task [4, 5]. A method with the same aim as the method presented in this work was presented in [3], but lacked a crucial step for accurate results.

SUMMARY

When tissues are imaged by a conventional CT system, they end up being displayed with a (gray scale) pixel value in typical ranges for each tissue. With the advent of spectral CT technologies it would be desirable to emulate conventional CT images with the same characteristic (gray scale) values for all relevant tissues, in order to ease technological transition.

For a given tissue, the range of typical gray scale values in a conventional CT image depends on the material itself, on system parameters, but also on object parameters such as size and presence of highly attenuating tissue. Spectral CT technology is able to remove the dependency on object parameters. In order to benefit from this and also mimic a conventional system, it is therefore necessary to derive a material specific (gray scale) value that only depends on system parameters. By way of example, a natural way to do so is to consider a thin sample, where the resulting value is referred to as an ideal Hounsfield unit.

Spectral CT data can be used to perform so-called basis decomposition. In theory it can be shown that the resulting data set can be weighted in a specific way to reproduce the ideal Hounsfield unit for all tissues, in effect mimicking a conventional CT system. In practice it turns out that the standard choice of using two basis functions to represent tissue in the basis decomposition results in biased (gray scale) values, and therefore not an accurate reproduction of ideal Hounsfield units.

This can at least partially be resolved by increasing the number of basis functions, but this is not a satisfactory solution because it also increases noise. What the inventor realized was that by the introduction of a calibration measurement of a phantom including reference materials such as water and air, the bias can be considered in the representative (gray scale) value computation and an accurate reproduction of ideal Hounsfield units can be achieved also when using a smaller number of basis functions such as two basis functions.

The method enables the emulation of many different system parameters of conventional CT systems. A radiologist familiar with a specific set of parameters can choose to emulate that specific set, while also benefitting from image quality improvements made possible by spectral CT technology.

According to the proposed technology, there is provided a method and corresponding arrangement for providing or reconstructing an image based on image data from an x-ray detector. In other words, there is provided a method and system for image reconstruction.

According to a first aspect, there is provided a method for reconstructing an image based on spectral image data acquired for at least two different effective energies. The method comprises obtaining a first set of spectral image data related to an object to be imaged and a second set of spectral image data related to a calibration phantom including at least one reference material. The method also comprises performing basis decomposition based on the first set of spectral image data to provide estimated basis images of the object to be imaged with respect to associated basis functions, and performing basis decomposition based on the second set of spectral image data to provide calibrated estimates of reference basis coefficients corresponding to said at least one reference material. Further, the method comprises determining image values representing the object to be imaged based on a system model of an imaging system to be emulated, the estimated basis images and their associated basis functions, and the calibrated estimates of reference basis coefficients.

According to a second aspect, there is provided an arrangement configured to reconstruct an image based on spectral image data acquired for at least two different effective energies. The arrangement is configured to obtain a first set of spectral image data related to an object to be imaged and a second set of spectral image data related to a calibration phantom including at least one reference material. The arrangement is configured to perform basis decomposition based on the first set of spectral image data to provide estimated basis images of the object to be imaged with respect to associated basis functions. The arrangement is also configured to perform basis decomposition based on the second set of spectral image data to provide calibrated estimates of reference basis coefficients corresponding to said at least one reference material. Further, the arrangement is configured to determine image values representing the object to be imaged based on a system model of an imaging system to be emulated, the estimated basis images and their associated basis functions, and the calibrated estimates of reference basis coefficients.

According to a third aspect, there is provided an x-ray imaging system comprising such an arrangement.

By way of example, the x-ray imaging system may be a CT system.

According to a fourth aspect, there is provided computer program comprising instructions, which when executed by at least one processor, cause the at least one processor to:
  obtain a first set of spectral image data related to an object to be imaged and a second set of spectral image data related to a calibration phantom including at least one reference material;
  perform basis decomposition based on the first set of spectral image data to provide estimated basis images of the object to be imaged with respect to associated basis functions;
  perform basis decomposition based on the second set of spectral image data to provide calibrated estimates of reference basis coefficients corresponding to said at least one reference material; and
  determine image values representing the object to be imaged based on a system model of an imaging system to be emulated, the estimated basis images and their associated basis functions, and the calibrated estimates of reference basis coefficients.

According to a fifth aspect, there is provided a corresponding computer-program product.

Other advantages will be appreciated when reading the detailed description.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

For a better understanding of the proposed technology it may be useful to start by briefly describing a non-limiting example of an imaging system.

Figure 1:
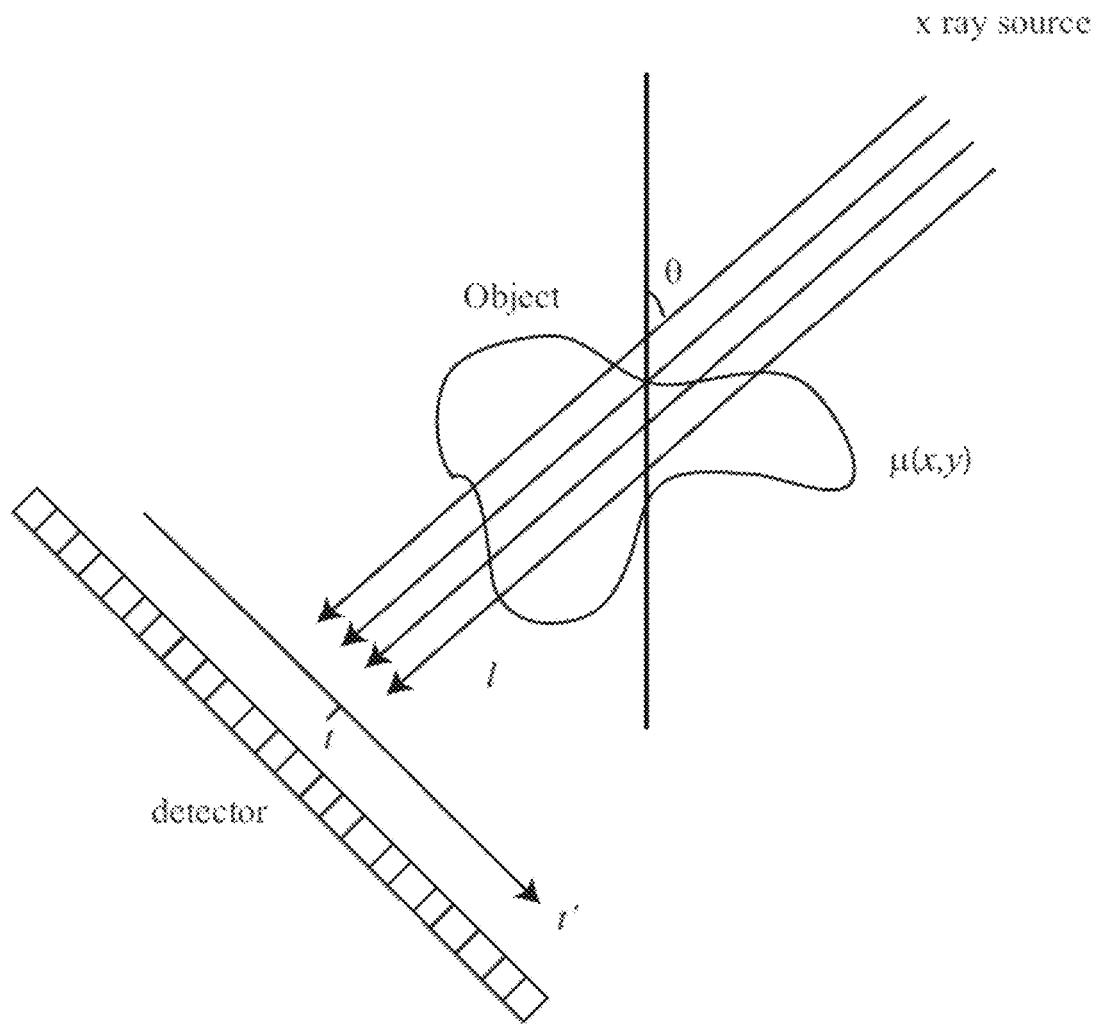
FIG. 1 is a schematic diagram illustrating an example of an imaging system setup showing projection lines from a source through an object to a detector.

FIG. 1 is a schematic diagram illustrating an example of an imaging system setup showing projection lines from a source through an object to a detector.

Figure 2:
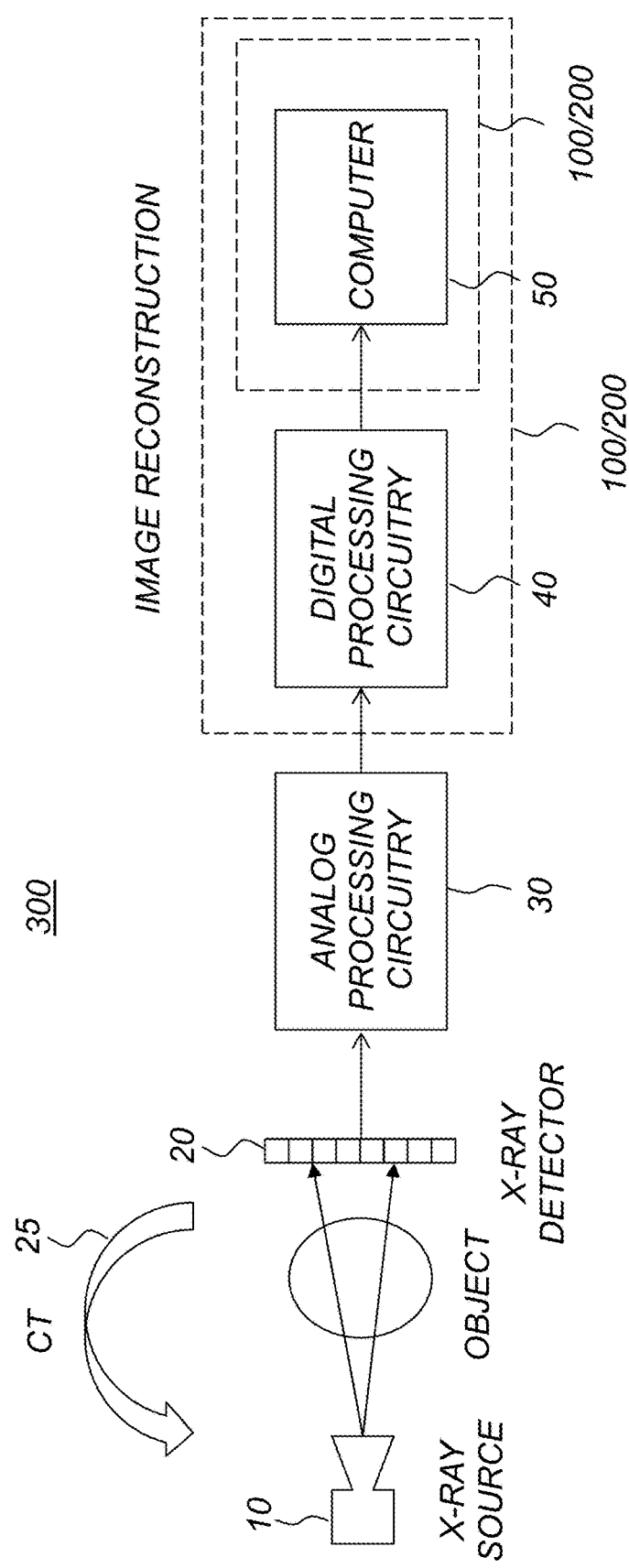
FIG. 2 is a schematic diagram illustrating an example of an x-ray imaging system.

As illustrated in the example of FIG. 2, an x-ray imaging system comprises an x-ray source 10, which emits x-rays; an x-ray detector 20, which detects the x-rays after they have passed through the object; analog processing circuitry 30, which processes the raw electrical signal from the detector and digitizes it; digital processing circuitry 40 which may carry out further processing operations on the measured data such as applying corrections, storing it temporarily, or filtering; and a digital computer 50 which stores the processed data and may perform further post-processing and/or image reconstruction. The overall detector may be regarded as the x-ray detector 20, or the x-ray detector 20 combined with the associated analog processing circuitry 30. The digital part including the digital processing circuitry 40 and/or the computer 50 may be regarded as an image reconstruction system 100/200, which performs image reconstruction based on the image data from the x-ray detector. The image reconstruction system 100/200 may thus be seen as the computer 50, or alternatively the combined system of the digital processing circuitry 40 and the computer 50, or possibly the digital processing circuitry 40 by itself if the digital processing circuitry is further specialized also for image reconstruction. The x-ray source 10 and/or the x-ray detector 20 may be arranged as part of a Computed Tomography (CT) system, e.g. mountable in a CT gantry.

Figure 3:
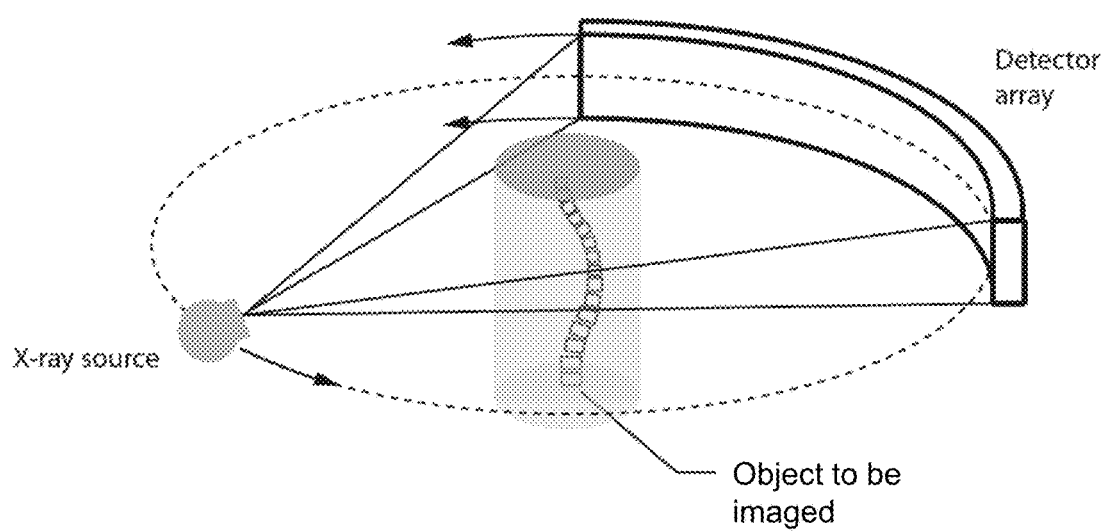
FIG. 3 is a schematic diagram illustrating a particular example of an x-ray system.

FIG. 3 is a schematic diagram illustrating a particular example of an x-ray system. In this example, the system comprises an x-ray source and an x-ray detector assembly mounted on a gantry that can be rotated with respect to a patient table. For example, the configuration may be based on a CT scanner equipped with photon-counting x-ray detectors. By way of example, the x-ray detector assembly can have the general configuration as disclosed in U.S. Pat. No. 8,183,535 B2.

In the following the proposed technology will be described with reference to non-limiting examples of implementation.

The various implementations of spectral CT can be divided into two categories, ones that can perform material basis decomposition in the projection domain and ones that can only do it in the image domain. The following example applies to the former category.

In this particular example, a theoretical framework will be presented. The framework starts by introducing a derivation of a quantity to mimic or emulate.

Ideal Hounsfield Units

Conventional x-ray CT images are typically displayed in Hounsfield Units, defined as:

$$HU(x) = 1000 \frac{\mu_{eff}(x) - \mu_{eff}^{water}}{\mu_{eff}^{water} - \mu_{eff}^{air}}, \quad (1.1)$$

where $\mu_{eff}(x)$ is the effective linear attenuation coefficient of the tissue or material in a pixel x and $\mu_{eff}^{water}$ and $\mu_{eff}^{air}$ are the effective linear attenuation coefficients of water and air determined for the particular system. These quantities are derived from the negative logarithm of conventional x-ray detector measurement data:

$$p(l) = -\log \frac{I(l)}{I_0(l)}, \quad (1.2)$$

where l denotes a projection line and $I(l)$ and $I_0(l)$ denote the measured signal in that projection line with and without an object present, respectively.

In medical x-ray imaging, tissues are characterized by their energy-dependent linear attenuation coefficient $\mu(E)$. An imaged object can therefore be represented by a spatial distribution of linear attenuation coefficients $\mu(x,E)$. The measured signal without an object is given by the integral of an energy-dependent function $w_1(E)$ (of a system to be emulated) determined by system parameters, $$I_0(l) = \int_0^\infty w_l(E) dE. \tag{1.3}$$

A typical model for $w_l(E)$ is $$w_l(E) = N_l(E) DE(E) R(E), \tag{1.4}$$

where $N_l(E)$ denotes the number of incident photons with energy E in the projection line l, $DE(E)$ denotes the detection efficiency of the detector, $R(E)$ denotes the detector response function, which for energy integrating systems is equal to the photon energy E. Other effects may be also be modeled in $w_l$. With an object present in the x-ray beam, the Lambert-Beer law states that the measured signal is given by:

$$I(l) = \int_0^\infty w_l(E) \exp(-\int_l \mu(x(s),E) ds) dE, \tag{1.5}$$

where $\int_l \mu(x(s),E) ds$ denotes the line integral of $\mu(x,E)$ along the projection line l. The effective linear attenuation coefficient $\mu_{eff}(x)$ in (1.1) is defined as the inverse projection of the projection data, i.e. a spatial function that for each projection line l satisfies:

$$p(l) = \int_l \mu_{eff}(x(s)) ds. \tag{1.6}$$

In two dimensions $\mu_{eff}(x)$ is given by the well-known inverse Radon transform of the projection data. It can be shown that for any given projection line l that there is an effective energy $E_{eff}$ such that:

$$\int_l \mu_{eff}(x(s)) ds = \int_l \mu(x(s), E_{eff}) ds. \tag{1.7}$$

The effective energy $E_{eff}$ depends on system parameters but also on the object because of so-called beam hardening. Projection lines passing through highly attenuating materials or very thick objects will be reconstructed at higher effective energies, causing artifacts in the reconstructed image.

Typically, methods for beam hardening artifact removal are applied to the reconstructed image. A suitable quantity to mimic would be the effective linear attenuation coefficient in the absence of beam hardening effects, in the sense of imaging a very thin sample of tissue. A straightforward way to derive this quantity is to consider a one-dimensional sample consisting of a single material with linear attenuation coefficient $\mu(E)$ and thickness $\Delta l$ in the limit as $\Delta l$ goes to zero. The ideal effective linear attenuation coefficient is thus defined as:

$$\mu_{eff}^* = \lim_{\Delta l \to 0} \frac{p(l)}{\Delta l}. \tag{1.8}$$

This quantity depends only on system parameters contained in $w_l(E)$ and the material specific $\mu(E)$, not on any other object parameters. By (1.2), (1.3) and (1.5) it follows that:

$$\lim_{\Delta l \to 0} \frac{p(l)}{\Delta l} = \lim_{\Delta l \to 0} -\frac{1}{\Delta l} \log\left( \frac{\int_0^\infty w_l(E) e^{-\mu(E)\Delta l} dE}{\int_0^\infty w_l(E) dE} \right) \tag{1.9}$$

-continued $$\stackrel{a)}{=} \lim_{\Delta l \to 0} -\frac{1}{\Delta l} \log\left( \frac{\int_0^\infty w_l(E)(1 - \mu(E)\Delta l + o(\Delta l)) dE}{\int_0^\infty w_l(E) dE} \right)$$

$$= \lim_{\Delta l \to 0} -\frac{1}{\Delta l} \log\left( 1 - \frac{\int_0^\infty w_l(E) \mu(E) \Delta l dE}{\int_0^\infty w_l(E) dE} + o(\Delta l) \right)$$

$$\stackrel{b)}{=} \lim_{\Delta l \to 0} \frac{1}{\Delta l} \left( \frac{\int_0^\infty w_l(E) \mu(E) \Delta l dE}{\int_0^\infty w_l(E) dE} + o(\Delta l) \right)$$

$$= \lim_{\Delta l \to 0} \left( \frac{\int_0^\infty w_l(E) \mu(E) dE}{\int_0^\infty w_l(E) dE} + o(1) \right) = \frac{\int_0^\infty w_l(E) \mu(E) dE}{\int_0^\infty w_l(E) dE}.$$

In steps a) and b) we use the standard Taylor expansions:

$$e^x \stackrel{a)}{=} 1 + x + o(x), \quad \log(1+x) \stackrel{b)}{=} x + o(x) \tag{1.10}$$

where the $o(x)$ comprises terms that vanish faster than x as x tends to zero. Thus $$\mu_{eff}^* = \frac{\int_0^\infty w_l(E) \mu(E) dE}{\int_0^\infty w_l(E) dE}. \tag{1.11}$$

For compact notation we define the normalized weighted inner product of a function $f$ with a weighting function $w$ as:

$$\langle f \rangle_w = \frac{\int_0^\infty f(E) w(E) dE}{\int_0^\infty w(E) dE} \tag{1.12}$$

With this notation, the ideal effective linear attenuation coefficient is given by:

$$\mu_{eff}^* = \langle \mu \rangle_w \tag{1.13}$$

and a corresponding ideal Hounsfield unit for a given tissue can be computed analogous to (1.1) as:

$$HU_w^* = 1000 \frac{\langle \mu \rangle_w - \langle \mu^{water} \rangle_w}{\langle \mu^{water} \rangle_w - \langle \mu^{air} \rangle_w}. \tag{1.14}$$

The aim of the following steps is the computation of an image that displays tissues in their ideal Hounsfield unit.

Basis Decomposition

Spectral CT data can be used to perform so-called basis decomposition [1, 6]. By assuming that the set of linear attenuation coefficients present in the imaged object is spanned by a smaller set of basis functions, the linear attenuation coefficient distribution $\mu(x,E)$ can be decomposed into:

$$\mu(x, E) = \sum_{k=0}^{K} a_k(x) f_k(E), \quad (1.15)$$

where $f_k(E)$ denotes the kth basis function and $\alpha_k(x)$ the corresponding spatial basis coefficient distribution, also referred to as basis image. Basis image estimates $\hat{\alpha}_k(x)$ can be obtained e.g. by maximum likelihood methods [2, 6].

By applying (1.13) to (1.15), it follows that the ideal effective linear coefficient distribution is given by:

$$\mu_{eff}^*(x) = \langle \mu(x, \cdot) \rangle_w = \left\langle \sum_{k=0}^{K} a_k(x) f_k(\cdot) \right\rangle_w = \sum_{k=0}^{K} a_k(x) \langle f_k \rangle_w \quad (1.16)$$

which implies that an estimate of $\mu_{eff}^*(x)$ can be obtained by forming the weighted sum of estimated basis images $\hat{\alpha}_k(x)$ with weights given by $\langle f_k \rangle_w$, where $f_k(E)$ is a known basis function and $w(E)$ models the system we want to mimic.

In ref [3] it was hypothesized that a spectral Hounsfield unit, also referred to as a synthetic Hounsfield unit, could be computed analogous to (1.1) as:

$$SHU(x) = 1000 \frac{\sum_{k=0}^{K} \hat{a}_k(x) \langle f_k \rangle_w - \sum_{k=0}^{K} a_k^{water} \langle f_k \rangle_w}{\sum_{k=0}^{K} a_k^{water} \langle f_k \rangle_w - \sum_{k=0}^{K} a_k^{air} \langle f_k \rangle_w}. \quad (1.17)$$

where $\alpha_k^{water}$ and $\alpha_k^{air}$ are the known basis coefficients of water and air, determined from the known basis functions $f_k(E)$ and the known linear attenuation coefficients of water and air. In implementation it however turns out that (1.17) fails to replicate ideal Hounsfield units as given by (1.14), which brings us to the following modification.

Calibration

In implementation of basis decomposition algorithms it is common to choose two basis functions to span the set of tissues in the human body. It is a good choice in the sense that two basis functions approximate this set well, although not perfectly, and that choosing more basis functions results in noisier basis images [2]. In reality, more than two basis functions are needed to completely approximate the set. This has the effect that basis images obtained from a two-basis decomposition have a slight bias [2], which propagates to the proposed synthetic Hounsfield unit (1.17).

This can be resolved by increasing the number of basis functions, but this is normally not a satisfactory solution. What the inventor realized was that by the introduction of a calibration measurement of a phantom including reference material(s) such as water and air, basis coefficients of water and air that are in a sense equally biased as the basis images of the object can be obtained. Replacing $\alpha_k^{water}$ and $\alpha_k^{air}$ in (1.17) with corresponding estimates $\hat{\alpha}_k^{water}$ and $\hat{\alpha}_k^{air}$ results in a modified or calibrated synthetic Hounsfield unit:

$$SHU^*(x) = 1000 \frac{\sum_{k=0}^{K} \hat{a}_k(x) \langle f_k \rangle_w - \sum_{k=0}^{K} \hat{a}_k^{water} \langle f_k \rangle_w}{\sum_{k=0}^{K} \hat{a}_k^{water} \langle f_k \rangle_w - \sum_{k=0}^{K} \hat{a}_k^{air} \langle f_k \rangle_w}, \quad (1.18)$$

which accurately replicates the proposed ideal Hounsfield unit given by (1.14) for all tissues, also when using a smaller number of basis functions (e.g. two basis functions).

In practice, this theoretical framework may for example be realized as or translated into a method and corresponding system for determining image (gray scale) values in the following way.

Figure 4:
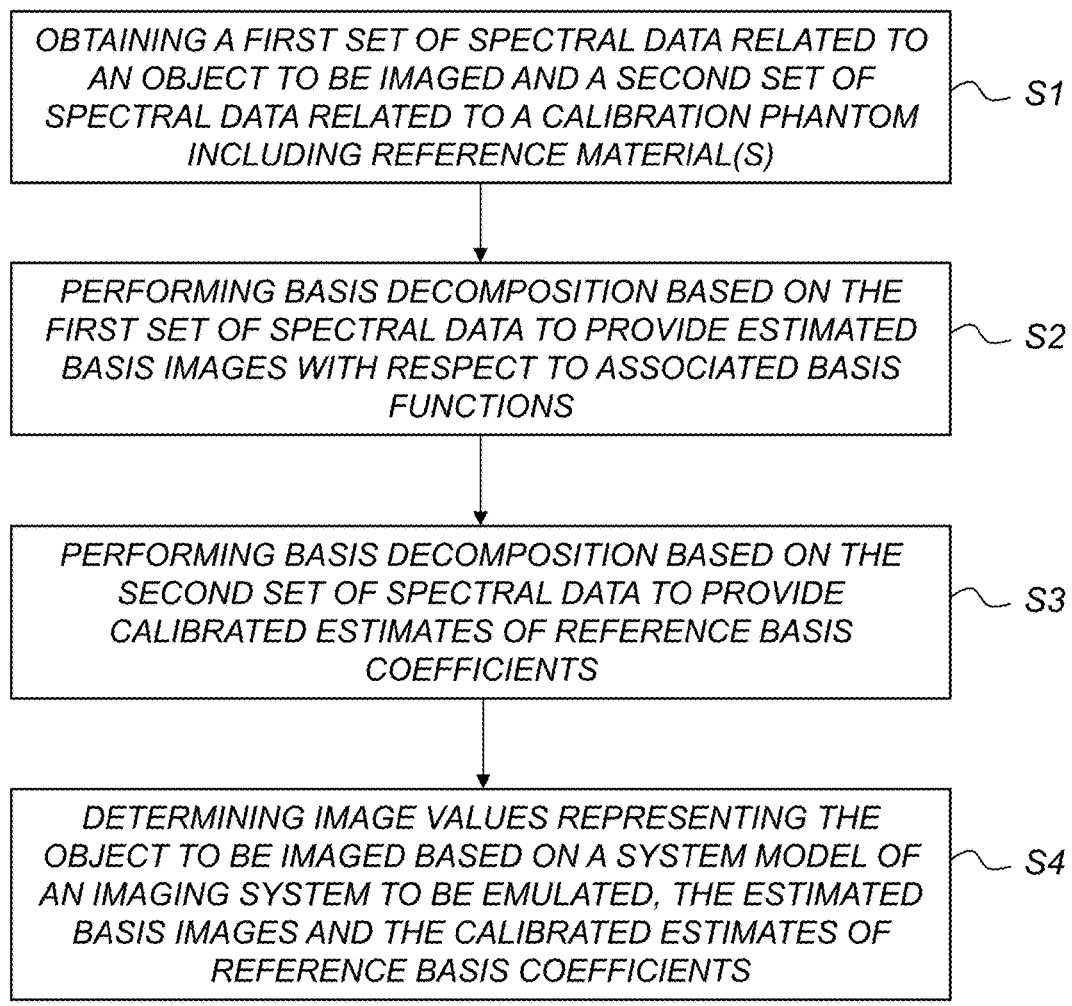
FIG. 4 is a schematic flow diagram illustrating an example of a method for image reconstruction according to an embodiment.

FIG. 4 is a schematic flow diagram illustrating an example of a method for image reconstruction according to an embodiment of a first aspect of the proposed technology. In this particular example, the method comprises the following steps:

S1: obtaining a first set of spectral image data related to an object to be imaged and a second set of spectral image data related to a calibration phantom including reference material(s);

S2: performing basis decomposition based on the first set of spectral image data to provide estimated basis images of the object to be imaged with respect to associated basis functions;

S3: performing basis decomposition based on the second set of spectral image data to provide calibrated estimates of reference basis coefficients corresponding to said at least one reference material; and S4: determining image values representing the object to be imaged based on a system model of an imaging system to be emulated, the estimated basis images and their associated basis functions, and the calibrated estimates of reference basis coefficients.

In step S1, the first set of spectral image data and the second set of spectral image data are preferably obtained from the same spectral imaging system.

It should be understood that the spectral image data may simply be provided as input for basis decomposition and imaging purposes.

By way of example, the spectral image data may be acquired from a spectral Computed Tomography, CT, system.

For example, the imaging system to be emulated may be a conventional non-spectral CT system.

In a particular example, the step S2 of performing basis decomposition based on the first set of spectral image data and/or the step S3 of performing basis decomposition based on the second set of spectral image data is/are performed using two basis functions.

As an example, the reference material(s) may include water and air, and the calibrated estimates of reference basis coefficients thus correspond to water and air. It should be understood that other types of suitable reference materials may be used.

In a particular example, the determined image values are represented by modified synthetic Hounsfield units.

For example, the modified synthetic Hounsfield units may be Hounsfield units determined based on basis decomposition and with respect to the calibrated estimates of reference basis coefficients.

It will be appreciated that the methods and arrangements described herein can be implemented, combined and re-arranged in a variety of ways.

For example, embodiments may be implemented in hardware, or in software for execution by suitable processing circuitry, or a combination thereof.

The steps, functions, procedures, modules and/or blocks described herein may be implemented in hardware using any conventional technology, such as discrete circuit or integrated circuit technology, including both general-purpose electronic circuitry and application-specific circuitry.

Alternatively, or as a complement, at least some of the steps, functions, procedures, modules and/or blocks described herein may be implemented in software such as a computer program for execution by suitable processing circuitry such as one or more processors or processing units.

Examples of processing circuitry includes, but is not limited to, one or more microprocessors, one or more Digital Signal Processors (DSPs), one or more Central Processing Units (CPUs), video acceleration hardware, and/or any suitable programmable logic circuitry such as one or more Field Programmable Gate Arrays (FPGAs), or one or more Programmable Logic Controllers (PLCs).

It should also be understood that it may be possible to re-use the general processing capabilities of any conventional device or unit in which the proposed technology is implemented. It may also be possible to re-use existing software, e.g. by reprogramming of the existing software or by adding new software components.

It is also possible to provide a solution based on a combination of hardware and software. The actual hardware-software partitioning can be decided by a system designer based on a number of factors including processing speed, cost of implementation and other requirements.

According to a second aspect, there is provided an arrangement configured to reconstruct an image based on spectral image data acquired for at least two different effective energies. The arrangement is configured to obtain a first set of spectral image data related to an object to be imaged and a second set of spectral image data related to a calibration phantom including at least one reference material. The arrangement is configured to perform basis decomposition based on the first set of spectral image data to provide estimated basis images of the object to be imaged with respect to associated basis functions. The arrangement is also configured to perform basis decomposition based on the second set of spectral image data to provide calibrated estimates of reference basis coefficients corresponding to said at least one reference material. Further, the arrangement is configured to determine image values representing the object to be imaged based on a system model of an imaging system to be emulated, the estimated basis images and their associated basis functions, and the calibrated estimates of reference basis coefficients.

By way of example, the arrangement may be configured to acquire the spectral image data from a spectral Computed Tomography, CT, system.

For example, the imaging system to be emulated may be a conventional non-spectral CT system.

In a particular example, the arrangement is configured to perform basis decomposition based on the first set of spectral image data and/or perform basis decomposition based on the second set of spectral image data, using two basis functions.

As an example, the reference material(s) may include water and air, and the arrangement is thus configured to provide calibrated estimates of reference basis coefficients corresponding to water and air.

In a particular example, the arrangement is configured to determine image values representing the object to be imaged in modified synthetic Hounsfield units.

For example, the modified synthetic Hounsfield units may be Hounsfield units determined based on basis decomposition and with respect to the calibrated estimates of reference basis coefficients.

Figure 5:
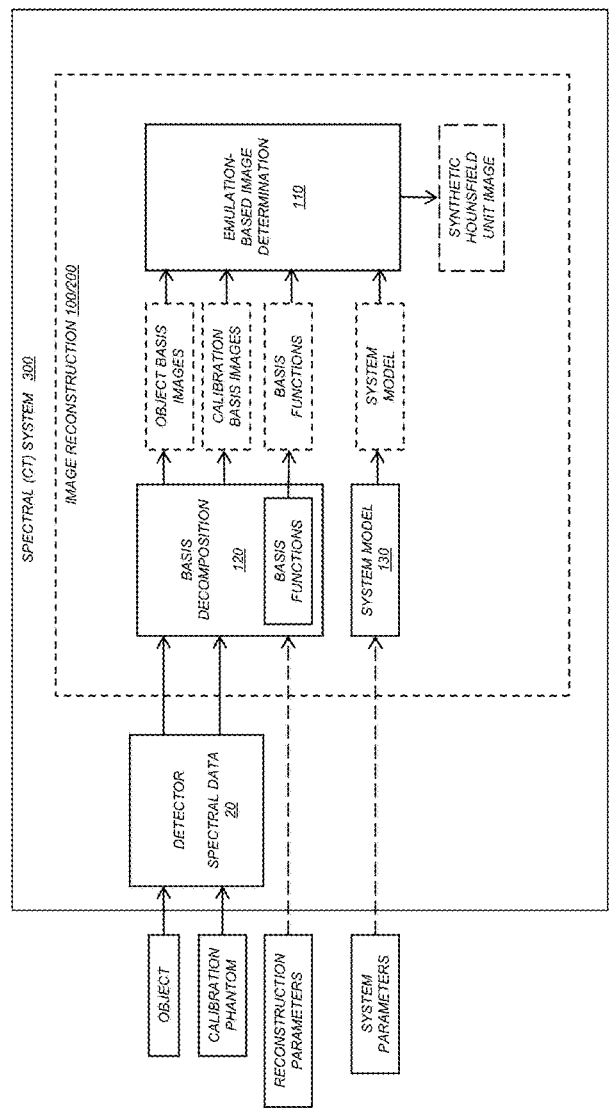
FIG. 5 is a schematic diagram illustrating an example of an overall system, also showing examples of inputs and outputs of the relevant sub-systems.

FIG. 5 is a schematic diagram illustrating an example of an overall system, also showing examples of inputs and outputs of the relevant sub-systems.

At the core, the system part for emulation-based image determination can be found, which is configured to perform step S4 defined above, e.g. to generate a modified synthetic Hounsfield unit image. In other words, an arrangement or module 110 for emulation-based image determination receives object basis images, calibration basis images or representations thereof (such as calibrated reference basis coefficients), as well as corresponding basis functions, and a system model describing the (conventional) system to be emulated as input for determining image values representing the object to be imaged.

An example of an overall image reconstruction system 100/200 normally comprises the above-described module 110 for emulation-based image determination, a module 120 for basis decomposition, and a module 130 for providing a system model. By way of example, the module 130 for providing a system model may be implemented as a system model library with associated data retrieving functionality for providing a model of the system to be emulated.

For example, the overall image reconstruction system 100/200 may be a computer-implementation, as will be described below.

FIG. 5 also schematically illustrates an example of an overall x-ray imaging system 300 such as a spectral CT system involving a detector 20 for obtaining spectral CT data based on x-ray measurements of an object and/or a calibration phantom. The spectral CT data may then be forwarded as input to the image reconstruction system 100/200.

Figure 6:
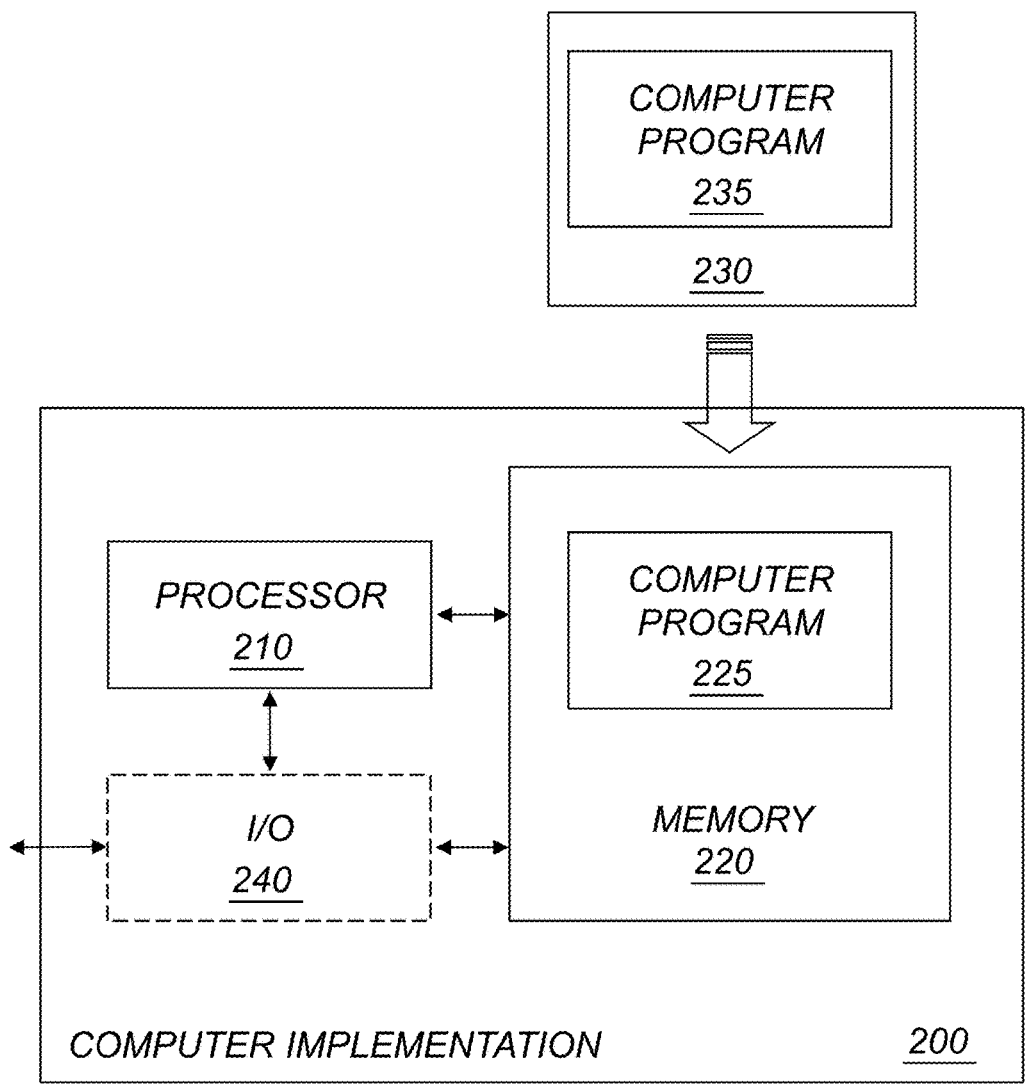
FIG. 6 is a schematic diagram illustrating an example of a computer-implementation according to an embodiment.

FIG. 6 is a schematic diagram illustrating an example of a computer-implementation 200 according to an embodiment. In this particular example, at least some of the steps, functions, procedures, modules and/or blocks described herein are implemented in a computer program 225; 235, which is loaded into the memory 220 for execution by processing circuitry including one or more processors 210. The processor(s) 210 and memory 220 are interconnected to each other to enable normal software execution. An optional input/output device 240 may also be interconnected to the processor(s) 210 and/or the memory 220 to enable input and/or output of relevant data such as input parameter(s) and/or resulting output parameter(s).

The term 'processor' should be interpreted in a general sense as any system or device capable of executing program code or computer program instructions to perform a particular processing, determining or computing task.

The processing circuitry including one or more processors 210 is thus configured to perform, when executing the computer program 225, well-defined processing tasks such as those described herein.

In particular, the memory 220 comprises instructions, which when executed by the at least one processor 210, cause the at least one processor 210 to reconstruct the image based on spectral image data.

Accordingly, there is provided a computer program 225; 235 comprising instructions, which when executed by at least one processor 210, cause the at least one processor 210 to:

obtain a first set of spectral image data related to an object to be imaged and a second set of spectral image data related to a calibration phantom including at least one reference material;

perform basis decomposition based on the first set of spectral image data to provide estimated basis images of the object to be imaged with respect to associated basis functions;

perform basis decomposition based on the second set of spectral image data to provide calibrated estimates of reference basis coefficients corresponding to said at least one reference material; and determine image values representing the object to be imaged based on a system model of an imaging system to be emulated, the estimated basis images and their associated basis functions, and the calibrated estimates of reference basis coefficients.

The processing circuitry does not have to be dedicated to only execute the above-described steps, functions, procedure and/or blocks, but may also execute other tasks.

The proposed technology also provides a computer program product comprising a computer-readable storage medium carrying the computer program described herein.

By way of example, the software or computer program 225; 235 may be realized as a computer program product, which is normally carried or stored on a computer-readable medium 220; 230, in particular a non-volatile medium. The computer-readable medium may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program may thus be loaded into the operating memory of a computer or equivalent processing device for execution by the processing circuitry thereof.

The procedural flows presented herein may be regarded as a computer flows, when performed by one or more processors. A corresponding apparatus may be defined as a group of function modules, where each step performed by the processor corresponds to a function module. In this case, the function modules are implemented as a computer program running on the processor.

The computer program residing in memory may thus be organized as appropriate function modules configured to perform, when executed by the processor, at least part of the steps and/or tasks described herein.

The embodiments described above are merely given as examples, and it should be understood that the proposed technology is not limited thereto. It will be understood by those skilled in the art that various modifications, combinations and changes may be made to the embodiments without departing from the present scope as defined by the appended claims. In particular, different part solutions in the different embodiments can be combined in other configurations, where technically possible.

REFERENCES

[1] Alvarez, Robert E., and Albert Macovski, "Energy-selective reconstructions in x-ray computerised tomography." *Physics in medicine and biology* 21.5 (1976): 733.

[2] Alvarez, Robert E. "Dimensionality and noise in energy selective x-ray imaging." *Medical physics* 40.11 (2013): 111909.

[3] Bornefalk, Hans. "Synthetic Hounsfield units from spectral CT data." *Physics in medicine and biology* 57.7 (2012): N83.

[4] Holmes, David R., et al. "Evaluation of non-linear blending in dual-energy computed tomography." *European journal of radiology* 68.3 (2008): 409-413.

[5] Kim, Kyung Su, et al. "Image fusion in dual energy computed tomography for detection of hypervascular liver hepatocellular carcinoma: phantom and preliminary studies." *Investigative radiology* 45.3 (2010): 149-157.

[6] Schlomka, JPea, et al. "Experimental feasibility of multi-energy photon-counting K-edge imaging in pre-clinical computed tomography." *Physics in medicine and biology* 53.15 (2008): 4031.

The invention claimed is:

1. A method for reconstructing an image based on spectral image data acquired for at least two different effective energies, wherein the method comprises:

obtaining a first set of spectral image data related to an object to be imaged and a second set of spectral image data related to a calibration phantom including at least one reference material;

performing basis decomposition based on the first set of spectral image data to provide estimated basis images of the object to be imaged with respect to associated basis functions;

performing basis decomposition based on the second set of spectral image data to provide calibrated estimates of reference basis coefficients corresponding to said at least one reference material; and determining image values representing the object to be imaged based on a system model of an imaging system to be emulated, the estimated basis images and their associated basis functions, and the calibrated estimates of reference basis coefficients.

2. The method of claim 1, wherein the first set of spectral image data and the second set of spectral image data are obtained from the same spectral imaging system.

3. The method of claim 1, wherein the spectral image data is acquired from a spectral Computed Tomography, CT, system.

4. The method of claim 3, wherein the imaging system to be emulated is a conventional non-spectral CT system.

5. The method of claim 1, wherein the step of performing basis decomposition based on the first set of spectral image data and/or the step of performing basis decomposition based on the second set of spectral image data is/are performed using two basis functions.

6. The method of claim 1, wherein the at least one reference material includes water and air, and the calibrated estimates of reference basis coefficients correspond to water and air.

7. The method of claim 1, wherein the determined image values are represented by modified synthetic Hounsfield units.

8. The method of claim 7, wherein the modified synthetic Hounsfield units are Hounsfield units determined based on basis decomposition and with respect to the calibrated estimates of reference basis coefficients.

9. An image reconstruction system configured to reconstruct an image based on spectral image data acquired for at least two different effective energies, wherein the image reconstruction system is configured to obtain a first set of spectral image data related to an object to be imaged and a second set of spectral image data related to a calibration phantom including at least one reference material, wherein the image reconstruction system comprises:

a basis decomposition sub-system configured to perform basis decomposition based on the first set of spectral image data to provide estimated basis images of the object to be imaged with respect to associated basis functions, and configured to perform basis decomposition based on the second set of spectral image data to provide calibrated estimates of reference basis coefficients corresponding to said at least one reference material; and an image determination sub-system configured to determine image values representing the object to be imaged based on a system model of an imaging system to be emulated, the estimated basis images and their associated basis functions, and the calibrated estimates of reference basis coefficients.

10. The image reconstruction system of claim 9, wherein the image reconstruction system is configured to acquire the spectral image data from a spectral Computed Tomography, CT, system.

11. The image reconstruction system of claim 10, wherein the imaging system to be emulated is a conventional non-spectral CT system.

12. The image reconstruction system of claim 9, wherein the basis decomposition sub-system is configured to perform basis decomposition based on the first set of spectral image data and/or perform basis decomposition based on the second set of spectral image data, using two basis functions.

13. The image reconstruction system of claim 9, wherein the at least one reference material includes water and air, and the basis decomposition sub-system is configured to provide calibrated estimates of reference basis coefficients corresponding to water and air.

14. The image reconstruction system of claim 9, wherein the image determination sub-system is configured to determine image values representing the object to be imaged in modified synthetic Hounsfield units.

15. The image reconstruction system of claim 14, wherein the modified synthetic Hounsfield units are Hounsfield units determined based on basis decomposition and with respect to the calibrated estimates of reference basis coefficients.

16. The image reconstruction system of claim 9, wherein the image reconstruction system comprises at least one processor and memory, the memory comprising instructions, which when executed by the at least one processor, cause the at least one processor to reconstruct said image based on spectral image data.

17. An x-ray imaging system comprising an image reconstruction system according to claim 9.

18. The x-ray imaging system of claim 17, wherein the x-ray imaging system is a Computed Tomography, CT, system.

19. A computer-program product comprising a non-transitory computer-readable medium having stored thereon a computer program comprising instructions, which when executed by at least one processor, cause the at least one processor to:

obtain a first set of spectral image data related to an object to be imaged and a second set of spectral image data related to a calibration phantom including at least one reference material;

perform basis decomposition based on the first set of spectral image data to provide estimated basis images of the object to be imaged with respect to associated basis functions;

perform basis decomposition based on the second set of spectral image data to provide calibrated estimates of reference basis coefficients corresponding to said at least one reference material; and determine image values representing the object to be imaged based on a system model of an imaging system to be emulated, the estimated basis images and their associated basis functions, and the calibrated estimates of reference basis coefficients.

* * * * *